United States Patent [19]

Lukas

[11] Patent Number: 4,705,658
[45] Date of Patent: Nov. 10, 1987

[54] METHOD FOR DRYING GELATIN IN THE MANUFACTURE OF HARD SHELL GELATIN CAPSULES

[75] Inventor: Stephen Lukas, Harrow, Canada

[73] Assignee: Capsule Technology International, Ltd., Windsor, Canada

[21] Appl. No.: 849,057

[22] Filed: Apr. 7, 1986

[51] Int. Cl.⁴ .............................................. B29C 71/04
[52] U.S. Cl. ........................................ 264/25; 264/26; 264/297.8; 264/304; 264/348; 264/DIG. 37; 425/174.4; 432/6
[58] Field of Search ............... 425/174.8 E, 174.8 R, 425/174.4; 264/26, 303, 305, 307, 202, 297.8, 301, DIG. 37, DIG. 46, 25, 234, 237; 432/6

[56] References Cited

U.S. PATENT DOCUMENTS

| | | |
|---|---|---|
| 1,657,982 | 1/1928 | Wilkie et al. .................... 264/307 |
| 2,318,185 | 5/1943 | Schreyer ............................. 264/307 |
| 2,451,961 | 10/1948 | Landau ................................ 264/25 |
| 2,555,450 | 6/1951 | Lee ............................. 264/DIG. 46 |
| 2,603,741 | 7/1952 | Seifried et al. ............. 264/DIG. 46 |
| 3,424,109 | 1/1969 | Joffe et al. ....................... 425/174.4 |
| 3,519,517 | 7/1970 | Dench ................................. 264/26 |
| 3,617,588 | 11/1971 | Langman .............................. 264/25 |
| 3,794,453 | 2/1974 | Padilla et al. ....................... 264/301 |

Primary Examiner—Jeffery Thurlow
Attorney, Agent, or Firm—Gifford, Groh, VanOphem, Sheridan, Sprinkle and Dolgorukov

[57] ABSTRACT

A method and apparatus for drying gelatin in the manufacture of hard shell gelatin capsules. Pins on pin bars are dipped into the liquid gelatin and the pins are then irradiated with microwave energy until the gelatin dries. Thereafter, the pins are gradually cooled to ambient temperature and the gelatin capsule halves are then stripped from the pins in the conventional fashion.

8 Claims, 2 Drawing Figures

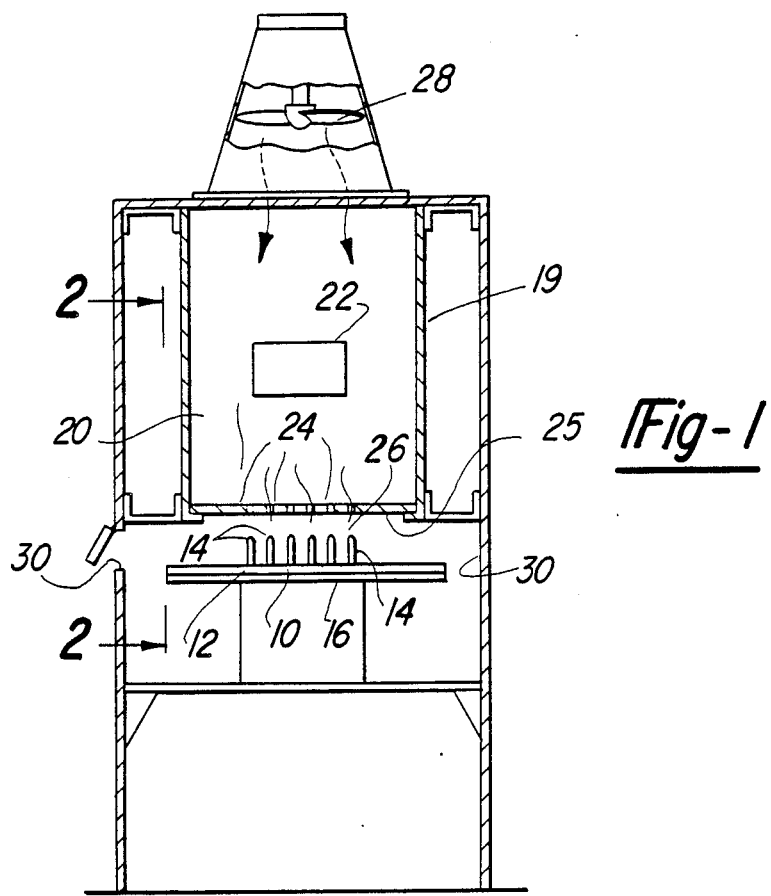
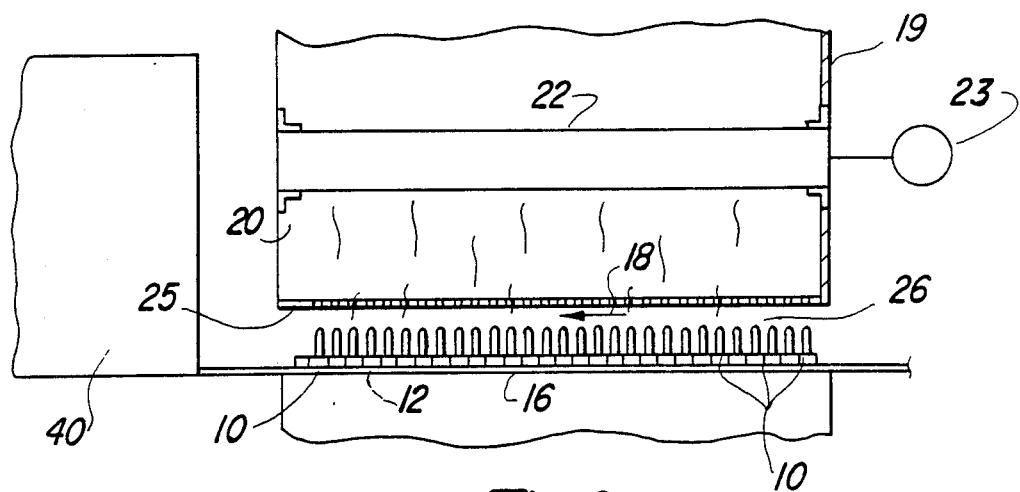

METHOD FOR DRYING GELATIN IN THE MANUFACTURE OF HARD SHELL GELATIN CAPSULES

BACKGROUND OF THE INVENTION

I. Field of the Invention

The present invention relates to a method and device for the manufacture of hard shell gelatin capsules.

II. Description of the Prior Art

In the manufacture of hard shell gelatin capsules, pin bars are conventionally dipped into liquid gelatin so that the outermost ends of the pins on the bars are covered with the gelatin. The pin bars are then conveyed along a track under carefully controlled temperature and humidity conditions until the gelatin has dried. The dried gelatin is then stripped from the pins thus forming either the capsule cap or the capsule body.

A primary disadvantage of these previously known machines for manufacturing the hard shell gelatin capsules is that the gelatin dries relatively slowly, oftentimes requiring thirty minutes or more before the gelatin is sufficiently dried so that it can be stripped from the pin bar. As such, the conveyor lines for the pin bars on which the pin bars are conveyed during this drying period, are necessarily lengthy thereby increasing the overall cost of the capsule manufacturing machinery.

SUMMARY OF THE PRESENT INVENTION

The present invention provides both a method and apparatus for drying gelatin in the manufacture of hard shell gelatin capsules.

In brief, after the pins on the pin bars are dipped into the liquid gelatin, the pins are irradiated with microwave energy until the gelatin dries. Thereafter, the pin bars together with the dried gelatin are gradually cooled to ambient temperature. The gelatin is then stripped from the pin bars thus forming the cap or body of the hard shell gelatin capsule.

In practice, it has been found that irradiating the gelatin with approximately 450 watts for the cap, or between 800 and 900 watts for the body (assuming 180 pins, each covered with gelatin) for a period of less than fifteen minutes is sufficient to dry the gelatin thereby reducing the required drying time by approximately 50% in comparison with the previously known methods.

BRIEF DESCRIPTION OF THE DRAWING

A better understanding of the present invention will be had upon reference to the following detailed description when read in conjunction with the accompanying drawing, wherein like reference characters refer to like parts throughout the several views, and in which:

FIG. 1 is a side diagrammatic view illustrating a preferred embodiment of the present invention; and FIG. 2 is a diagrammatic view taken substantially along line 2—2 in FIG. 1.

DETAILED DESCRIPTION OF A PREFERRED EMBODIMENT OF THE PRESENT INVENTION

With reference to the drawing, a portion of the apparatus for manufacturing hard shell gelatin capsules is thereshown and comprises a plurality of elongated pin bars 10 (FIG. 2) which are positioned in a side by side relationship to each other. Furthermore, as shown in FIG. 1, each pin bar 10 includes an elongated and generally flat base 12 and a plurality of spaced pins 14 extending upwardly from an upper surface of the base 12.

As best shown in FIG. 2, the pin bars 10 are supported on a conventional conveying surface 16 and are adapted to be driven in the direction of arrow 18 (FIG. 2). Furthermore, the upper or free ends of the pins 14 on the pin bars 10 are adapted to be dipped into liquid gelatin in the conventional fashion so that, after drying, the dried gelatin forms either the cap or body of a hard shell gelatin capsule.

Referring now to FIGS. 1 and 2, a housing 19 forms a plenum 20 directly above the pins 14 on the pin bars 10. This plenum 20 is open through a plurality of openings 24 in the bottom 25 of the housing 19 to the pins 14. Furthermore, a microwave wave guide 22 extends through the plenum 20 and a microwave energy generator 23 (FIG. 2) is coupled to the wave guide 22. Consequently, when activated, the microwave generator 23 generates microwave energy into the plenum 20, through openings 24 in the bottom 25 of the plenum 20 and thus to a chamber 26 surrounding the pins 14 on the pin bars 10.

With reference to FIG. 1, a fan 28 is also preferably mounted to the housing 19 so that, when activated, the fan 28 forces air from the plenum 20 through the openings 24 and into the capsule drying chamber 26. From the capsule drying chamber 26, the air exhausts through openings 30 formed in the side of the capsule drying chamber 26. The air flow through the capsule drying chamber 26 thus convectively removes moisture from the gelatin while, conversely, the microwave generator 23 removes moisture from the gelatin through radiant energy.

EXAMPLE 1

1. The pin bars containing 180 pins for hard shell gelatin capsule caps, after being dipped in liquid gelatin, were placed in the drying chamber 26 and a microwave generator 23 capable of generating between 430–450 watts of power was activated.

2. After eight minutes, the gelatin had dried.

EXAMPLE 2

1. The pin bars containing 180 pins for the body of the hard shell gelatin capsule were dipped into liquid gelatin and placed within the drying chamber 26. In the conventional fashion, the body of the capsule has an overall length, and thus an overall mass, greater than the cap of the capsule.

2. The microwave generator 23 having a power output of between 800 and 900 watts was then activated.

3. At thirteen minutes, the gelatin had dried.

Following drying of the gelatin for either the cap or the body, the pin 14 on the pin bars 10 were gradually cooled for a period of approximately five minutes until the pins with their components, i.e. either the cap or body, of the hard shell gelatin capsule attained ambient temperature. The pins were then stripped in the conventional fashion and the above process repeated.

It will be understood, of course, that the power of the microwave energy necessary to dry the capsules will vary depending upon the number of pins 14 on the pin bars 10.

Through experimentation, it has been found that it is necessary to gradually cool the pins 14 as well as the dried gelatin to substantially ambient temperature prior to stripping. Unless the pins and gelatin capsules are gradually cooled in this fashion, stripping of the pins while the gelatin is warm will result in wrinkling of the capsules which is unacceptable. Furthermore, rapid cooling of the pins following irradiation by the microwave energy is equally unacceptable since such rapid cooling has been found to cause the capsules to star end.

Preferably, such cooling takes place in a chamber 40 into which the pins 10 are moved by the conveying means 16 after passing under the plenum housing 19. The chamber 40 is substantially closed along the sides and top so that the capsules cool gradually.

In the preferred form of the invention, the pins 10 are constructed of stainless steel which is the same material that pins in the previously known hard shell gelatin capsule machines have been constructed. Consequently, no modification of the previously known pins are required.

Alternatively, however, the pns 10 are constructed of plastic or teflon coated metal pins.

In order to ensure substantially even drying of the capsules when subjected to microwave irradiation, the pins 14 are preferably moved in the direction of arrow 18 during the microwave irradiation process. In practice, it has been found that movement of the metal pins through the drying chamber 26 during microwave irradiation dispenses the microwave field within the drying chamber 26 and assures a substantially uniform distribution of the microwave energy. In doing so, local hot spots and uneven drying of the gelatin is avoided.

In practice, it has been found that the present invention reduces the time necessary to dry the gelatin on the pins by 50% or more when compared with the previously known devices. As such, the present invention reduces the overall length of the required conveyor mechanism by one-half or more of the previously known lengths.

Furthermore, it has been found that capsules dried in accordance with the present invention do not suffer any adverse effects over capsules dried in accordance with the previously known methods.

Having described my invention, however, many modifications thereto will become apparent to those skilled in the art to which it pertains without deviation from the spirit of the invention as defined by the scope of the appended claims.

I claim:

1. A method for drying gelatin on pins to form hard shell gelatin capsules comprising the steps of:
   irradiating the gelatin in a drying chamber with microwave energy for a time period sufficient to dry the gelatin,
   thereafter moving the pins to a substantially closed cooling chamber separate from the drying chamber so that the gelatin on the pins gradually cools to ambient temperature, and
   then stripping the solidified gelatin from the pins.

2. The invention as defined in claim 1 wherein said pins are constructed of metal and further comprising the step of moving said pins during said irradiation step.

3. The invention as defined in claim 2 wherein said pins are constructed of stainless steel.

4. The invention as defined in claim 1 wherein the pins are constructed of plastic.

5. The invention as defined in claim 2 wherein the pins are constructed of metal having a teflon coating.

6. The invention as defined in claim 1 wherein said irradiating step comprises irradiating said pins with microwave power for a period of between 5 and 15 minutes.

7. The invention as defined in claim 4 wherein said cooling step extends over a period of not less than five minutes.

8. The invention as defined in claim 1 and further comprising the step of circulating air through said drying chamber.

* * * * *